United States Patent
Su

(10) Patent No.: US 9,572,971 B2
(45) Date of Patent: Feb. 21, 2017

(54) OSMOTIC ORTHODONTIC APPLIANCE

(71) Applicant: National Tsing Hua University, Hsinchu (TW)

(72) Inventor: Yu-Chuan Su, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 50 days.

(21) Appl. No.: 14/840,856

(22) Filed: Aug. 31, 2015

(65) Prior Publication Data
US 2016/0331950 A1 Nov. 17, 2016

(30) Foreign Application Priority Data
May 15, 2015 (TW) .............................. 104115593 A

(51) Int. Cl.
| | | |
|---|---|---|
| A61C 7/08 | (2006.01) | |
| A61C 7/10 | (2006.01) | |
| A61M 39/00 | (2006.01) | |
| A61C 7/00 | (2006.01) | |

(52) U.S. Cl.
CPC ................ *A61M 39/00* (2013.01); *A61C 7/08* (2013.01); *A61C 7/10* (2013.01); *A61C 7/00* (2013.01); *A61M 2205/0216* (2013.01); *A61M 2210/0637* (2013.01)

(58) Field of Classification Search
CPC ............. A61C 7/282; A61C 7/28; A61C 7/08; A61C 7/10; A61M 31/002; A61M 2039/0297; A61M 2210/0637
See application file for complete search history.

(56) References Cited

U.S. PATENT DOCUMENTS

| | | | | |
|---|---|---|---|---|
| 3,494,034 A * | 2/1970 | Kesling | .................. | A61C 7/282 433/17 |
| 3,995,631 A * | 12/1976 | Higuchi | .................. | A01G 7/06 222/95 |
| 4,203,440 A * | 5/1980 | Theeuwes | .............. | A61K 9/009 222/386.5 |
| 4,203,442 A * | 5/1980 | Michaels | ............ | A61M 31/002 424/423 |
| 4,320,759 A * | 3/1982 | Theeuwes | ........... | A61M 31/002 424/424 |
| 5,980,508 A * | 11/1999 | Cardamone | ......... | A61M 31/002 604/890.1 |
| 6,491,519 B1 * | 12/2002 | Clark | ....................... | A61C 7/00 433/18 |

(Continued)

FOREIGN PATENT DOCUMENTS

WO WO 03086526 A1 * 10/2003

*Primary Examiner* — Cris L Rodriguez
*Assistant Examiner* — Stephen Sparks
(74) *Attorney, Agent, or Firm* — WPAT, P.C., Intellectual Property Attorneys; Anthony King

(57) ABSTRACT

The present invention provides an osmotic orthodontic appliance, comprising: an actuation structure forming a hollow tube filled with a supersaturated solution; a dental aligner structure mounted on the actuation structure for fixing the actuation structure on teeth; and a pumping structure connected one end of the hollow tube, comprising a semipermeable device and a supporting structure. The osmotic orthodontic appliance of the present invention could provide steady movement and force output; it is a solution for the periodic actuation problem of conventional orthodontic appliances.

9 Claims, 7 Drawing Sheets

(56) References Cited

U.S. PATENT DOCUMENTS

| | | | | |
|---|---|---|---|---|
| 6,533,579 B2* | 3/2003 | Komiyama | ............ | A61J 7/0092 |
| | | | | 433/80 |
| 6,984,128 B2* | 1/2006 | Breining | .................. | A61C 7/00 |
| | | | | 433/24 |
| 7,252,506 B2* | 8/2007 | Lai | ........................... | A61C 7/20 |
| | | | | 433/20 |
| 8,882,499 B2* | 11/2014 | White | ....................... | A61C 7/00 |
| | | | | 433/18 |
| 2005/0277084 A1* | 12/2005 | Cinader | .................... | A61C 7/20 |
| | | | | 433/20 |
| 2011/0007920 A1* | 1/2011 | Abolfathi | ............. | H04R 25/606 |
| | | | | 381/326 |

* cited by examiner

OSMOTIC ORTHODONTIC APPLIANCE

CROSS-REFERENCE TO RELATED APPLICATION

This application claims the priority of Taiwanese patent application No. 104115593, filed on May 15, 2015, which is incorporated herewith by reference.

BACKGROUND OF THE INVENTION

1. Field of the Invention

The present invention relates to an orthodontic appliance, and more particularly relates to an osmotic orthodontic appliance which generates a predetermined deformation by osmotic pressure to give the teeth constant orthodontic force.

2. The Prior Arts

With advances in medical technology, the problem of teeth alignment including crowding of teeth, spacing of teeth, cross bite, deep bite, open bite or scissors bite of teeth and etc., could be corrected by orthodontic treatment.

In addition to the basic chewing functions, dental and smile esthetics have been influencing self-image and self-confidence in people's quality of life as well. Everyone wants to have a charming smile whether in social or work situation, which usually brings us improvement on self-confidence and self-esteem. With the improvement of people's social well-being, more attention has been paid to the orthodontic enhancement.

The orthodontic appliance employed in orthodontic treatment facilitates the adjustment of teeth to their proper position. Conventional orthodontic appliance comprises a plurality of brackets with each fixed to corresponding tooth separately, and a metal wire connecting all the brackets. The tightness of the metal wire is adjusted time by time for aligning the teeth. However, the distress problem would be raised since the metal wire gives the highest stress right after every adjustment, while the user usually feel uncomfortable at this time, then the stress decreases since the teeth move until the next adjustment. Therefore, the user must experience many times of distress and chewing difficulty caused by the high stresses during orthodontic treatment, and such that the user loses his/her weight or feel uncomfortable in daily life (e.g. while sleeping).

In the design of orthodontic appliance, utilizing high elasticity material makes the user feels more comfortable, but aligning effect is not so well; in contrast, utilizing low elasticity material brings great aligning effect but makes the user feels uncomfortable and reduces the willingness to wear the appliance. Thus, how to balance the aligning effect and user's comfort is a great concern in current orthodontic therapy.

SUMMARY OF THE INVENTION

To solve the problem, the present invention provides an osmotic orthodontic appliance, comprising: an actuation structure forming a hollow tube filled with a supersaturated solution; a dental aligner structure mounted on the actuation structure for fixing the actuation structure on teeth; and a pumping structure connected with one end of the hollow tube, comprising a semipermeable device and a supporting structure, wherein the supporting structure supports the semipermeable device.

In an embodiment of the present invention, the hollow tube has a sealing coating on inner surface thereof, and the sealing coating is polydimethylsiloxane.

In an embodiment of the present invention, the actuation structure, the dental aligner structure and the pumping structure are made of a thermoplastic polymer material.

In an embodiment of the present invention, the semipermeable device is mainly a semipermeable membrane. The preferred semipermeable membrane is made of cellulose, aromatic polyamide, polyimide, polyfurane or thermoplastic polyurethane.

In an embodiment of the present invention, the actuation structure has a partially inflated structure.

According to the features of the present invention, the osmotic orthodontic appliance provides the user who receives orthodontic treatment a long-term, steady and adjustable force to align teeth, avoiding uncomfortable feeling in oral cavity and time delay to the treatment caused by the periodic force variation which jumps abruptly and drops slowly as in conventional orthodontic treatment. In addition, the osmotic orthodontic appliance of the present invention is transparent at daily exposed parts, such that the user's appearance is not affected during orthodontic treatment, and reduces inferiority feelings during orthodontic treatment.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1:
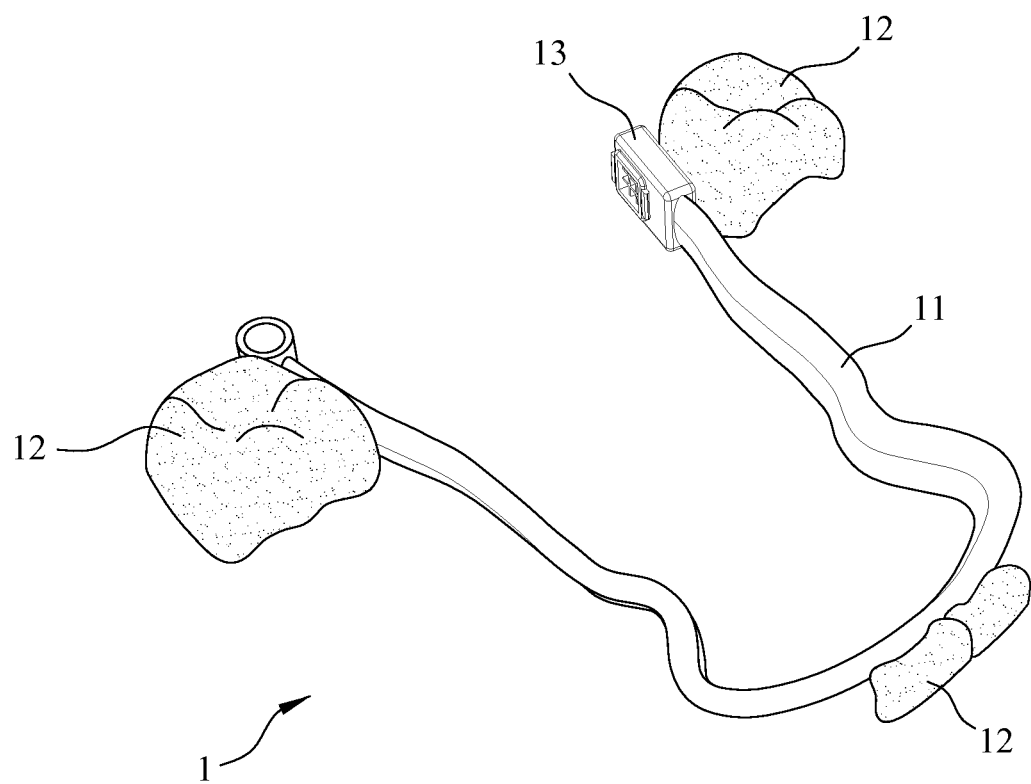
FIG. 1 shows a schematic diagram illustrating the osmotic orthodontic appliance according to one embodiment of the present invention.

Referring to FIG. 1, there is shown a schematic diagram illustrating the osmotic orthodontic appliance according to one embodiment of present invention. The osmotic orthodontic appliance 1 comprising an actuation structure 11 forming a hollow tube filled with a supersaturated solution; a dental aligner structure 12 mounted on the actuation structure 11 for fixing the actuation structure 11 on teeth; and a pumping structure 13 connected with one end of the hollow tube, comprising a semipermeable device 131 and a supporting structure 132, also shown in FIG. 3. Further, the osmotic orthodontic appliance 1 could comprise a plural of the pumping structure 13 connecting with the actuation structure 11, to provide enough osmotic pressure for allowing the actuation structure 11 to achieve the predetermined deformation or deformation speed.

Figure 2:
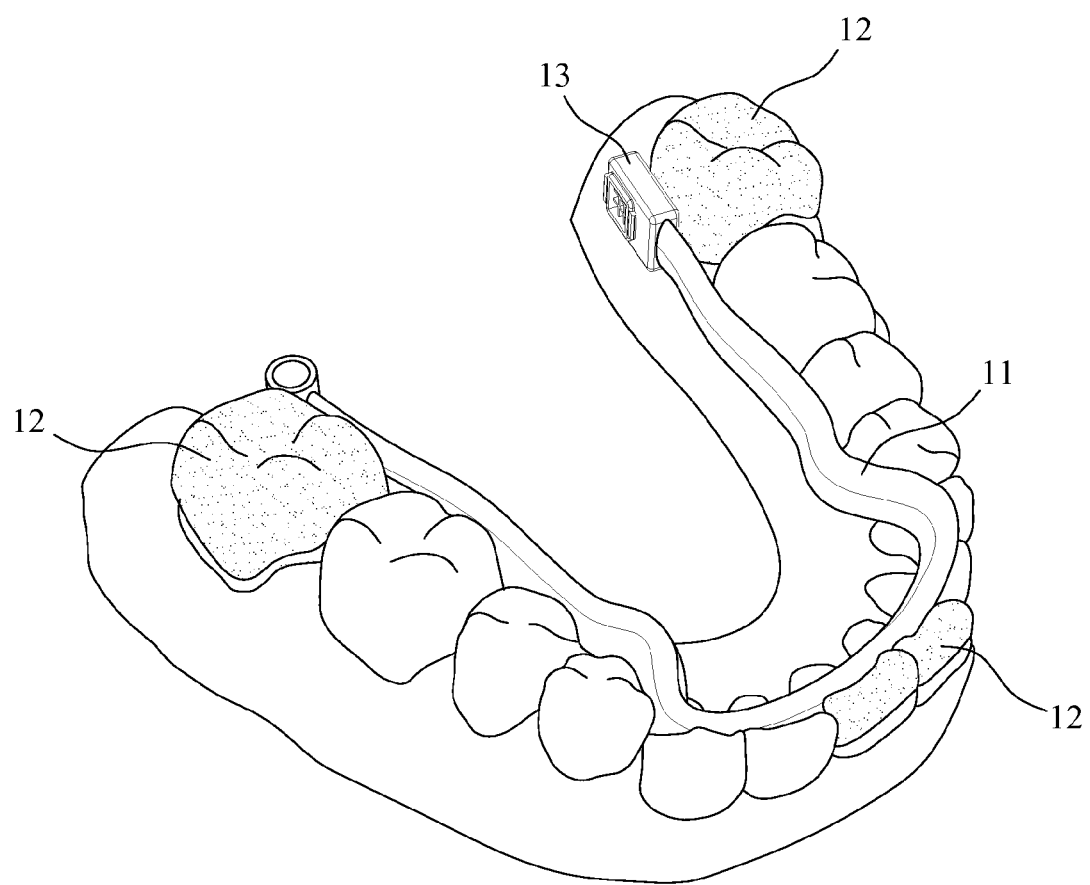
FIG. 2 shows a schematic diagram illustrating the osmotic orthodontic appliance used in orthodontic treatment.

Referring to FIG. 2, there is shown a schematic diagram illustrating the osmotic orthodontic appliance 1 used in orthodontic treatment. The actuation structure 11 is located on the inner side of teeth (also known as lingual side), thus the user has no change in appearance. The dental aligner structure 12 is mounted on the actuation structure 11 to fix the actuation structure 11 to specific teeth by encasing teeth according to their shape. The dental aligner structure 12 is used to fix the actuation structure 11 and to align specific teeth. In the preferred embodiment of the present invention, the dental aligner structure 12 which is anchored on molar teeth render the dental aligner structure 12 could be immovable around this portion since the molar teeth are not easy to move; and the dental aligner structure 12 encasing foretooth is used for strengthening the aligning effect around this portion or correcting the alignment of specific teeth. It is noted that the shape of the dental aligner structure 12 and the encased teeth are not limited to the figures showed in the drawings. The dental aligner structure 12 can be applied to any tooth. Further, the dental aligner structure 12 could be made of transparent material, thus the user's appearance is not affected during orthodontic treatment.

Figure 3A:
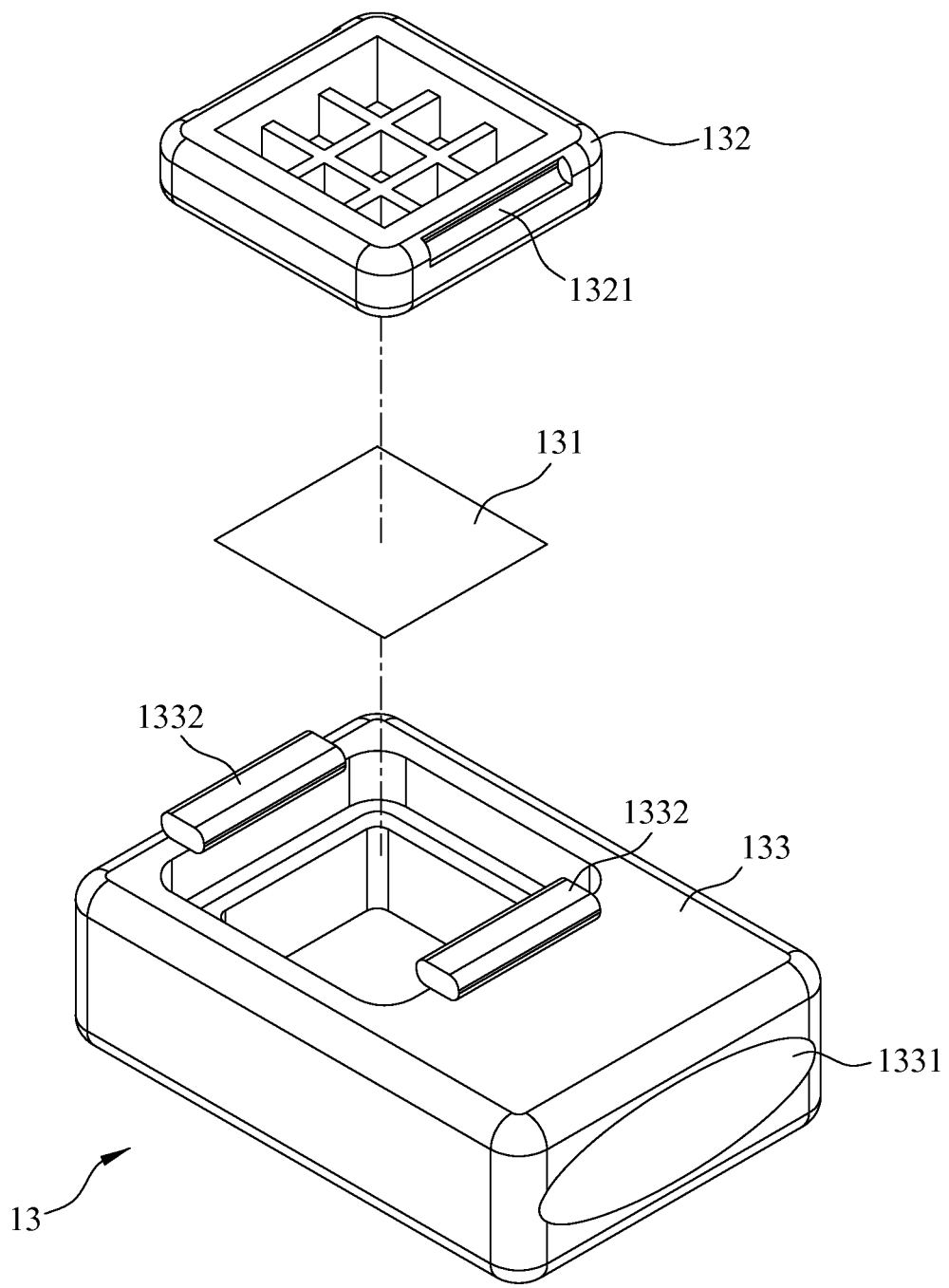
FIG. 3A shows a schematic diagram illustrating the components of the pumping structure.
Figure 3B:
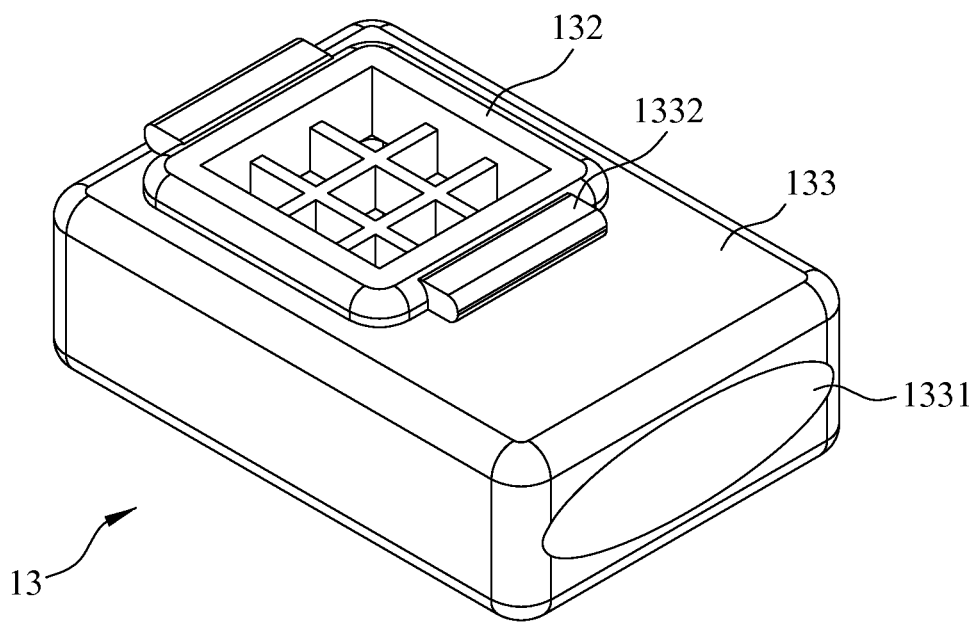
FIG. 3B shows a schematic diagram illustrating the pumping structure being assembled.

Referring to FIG. 3A, there is shown a schematic diagram illustrating the components of the pumping structure 13. The pumping structure 13 could comprise a semipermeable device 131, a supporting structure 132 and a body 133. The body 133 has an opening 1331 which connects to the actuation structure 11. The semipermeable device 131 is a device that allows water to pass through but the solute therein can't. Thus, the water in saliva passes through the semipermeable device 131 and flows into the actuation structure 11 through the opening 1331. The solute of supersaturated solution in actuation structure 11 does not flow to oral cavity since the semipermeable property of semipermeable device 131. In some embodiment, pumping structure 13 only comprises the semipermeable device 131, the semipermeable device 131 allows water to pass through but the solute therein doesn't, and could connect to the actuation structure 11 directly. FIG. 3B shows a schematic diagram illustrating the pumping structure 13 being assembled. In the more preferred embodiment of the present invention, the semipermeable device 131 is mainly a soft and flexible semi-permeable membrane, thus the supporting structure 132 and the body 133 is needed.

In an embodiment of the present invention, the semipermeable device 131 is mainly a semi-permeable membrane such as the membrane used in reverse osmosis water filters, and made of cellulose, aromatic polyamide, polyimide or polyfurane, for instance. Further, the semi-permeable membrane also could be made of polymer having waterproof breathable property, for instance, thermoplastic polyurethane (TPU) also having semi-permeable property.

The semi-permeable pumping structure 13 and the actuation structure 11 are integrated through assembly. The junction of the pumping structure 13 and the actuation structure 11 (i.e. the position of opening 1331) has a circle of soft and flexible material on its inner side to fill the interstice, and thereby avoiding leakage from the interstice which is generated by assembly. The soft and flexible material could be polydimethylsiloxane (PDMS). The supporting structure 132 mainly provides the semi-permeable membrane stable support.

The pumping structure 13 could have a mating male connection element 1332 of a snap-fit structure, and the supporting structure 132 has at least a groove 1321, served as a mating female connection element of the snap-fit structure. The shapes of the mating male connection element 1332 and the groove 1321 are in good match for each other, thus when assemble the semipermeable device 131 and the supporting structure 132 with the body 133, the mating male connection element 1332 could snap-fit into the groove 1321, thereby the joint will be fixed and sealed.

The actuation structure 11, the dental aligner structure 12 and the pumping structure 13 are made by 3D printing and made of thermoplastic polymers. The osmotic actuation structure 11 is hollow and could have a considerable degree of deformation, thus high toughness is needed and therefore it commonly made of polylactic acid (PLA). Further, to avoid the solution in the actuation structure 11 leaks from the defects made by 3D printing process, a soft and flexible material is used for pressure-assisted uniform coating on its inner surface as a sealing coating. The sealing coating comprises but not limited to polydimethylsiloxane (PDMS). Transparent dental aligner structure 12 is commonly made of polyurethane (PU). The multi-nozzle 3D printer is used to integrate the actuation structure 11 and the dental aligner structure 12 which are made of different materials, such combinative printing could generate results with integrally molded parts.

The inner space of the osmotic pumping structure 13 and the pressurized actuation structure 11 is filled with a supersaturated solution, which is a supersaturated aqueous solution of salt or sugar, for instance. The water in oral cavity permeates into a sealed structure (the osmotic pumping structure 13 and the pressurize actuation structure 11) since the concentration difference between two sides of the semipermeable device 131 (i.e., inner side and outer side of the pumping structure 13). The water permeation rate is dependent on the thickness and effective area of the semipermeable membrane. The concentration difference between inside and outside of the semipermeable device 131 would not change since the solution inside is always supersaturated, so the pumping rate of the pumping structure 13 is constant all the time. In addition, even there are resistances, the pumping rate would not change since the osmotic pressure is very high (up to tens or even hundreds of atmospheres). With the water entering continuously, the pressure inside the actuation structure 11 rises continuously and makes the steady deformation of the actuation structure 11.

Figure 4A:
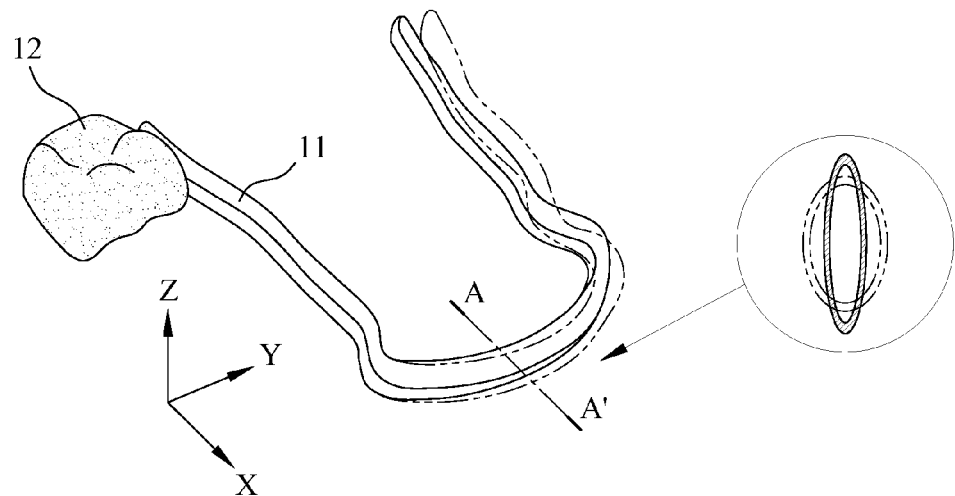
FIG. 4A shows a schematic diagram illustrating the major axis of cross-sectional ellipse set to Z axis, so the actuation structure will deform on XY plane.
Figure 4B:
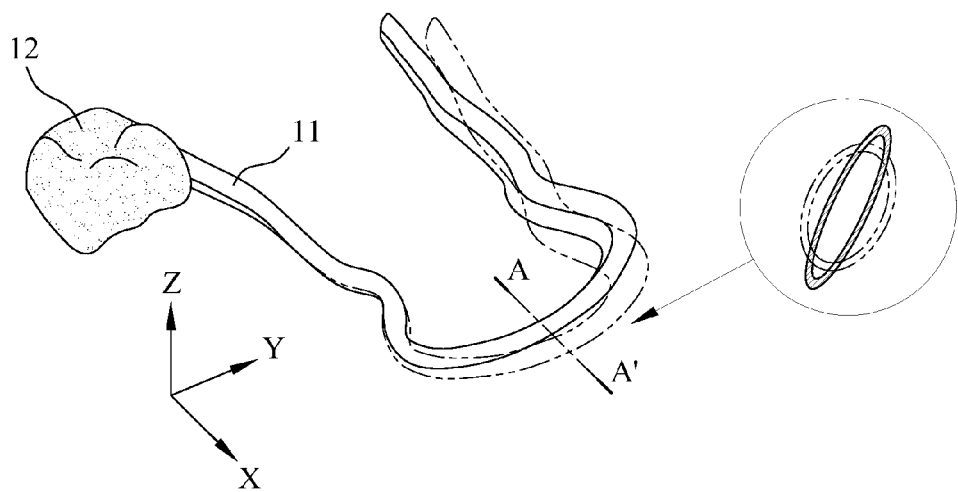
FIG. 4B shows a schematic diagram illustrating the major axis of cross-sectional ellipse set to a specific angle relative to Z axis, so the actuation structure will increase the deformation along Z axis.
Figure 4C:
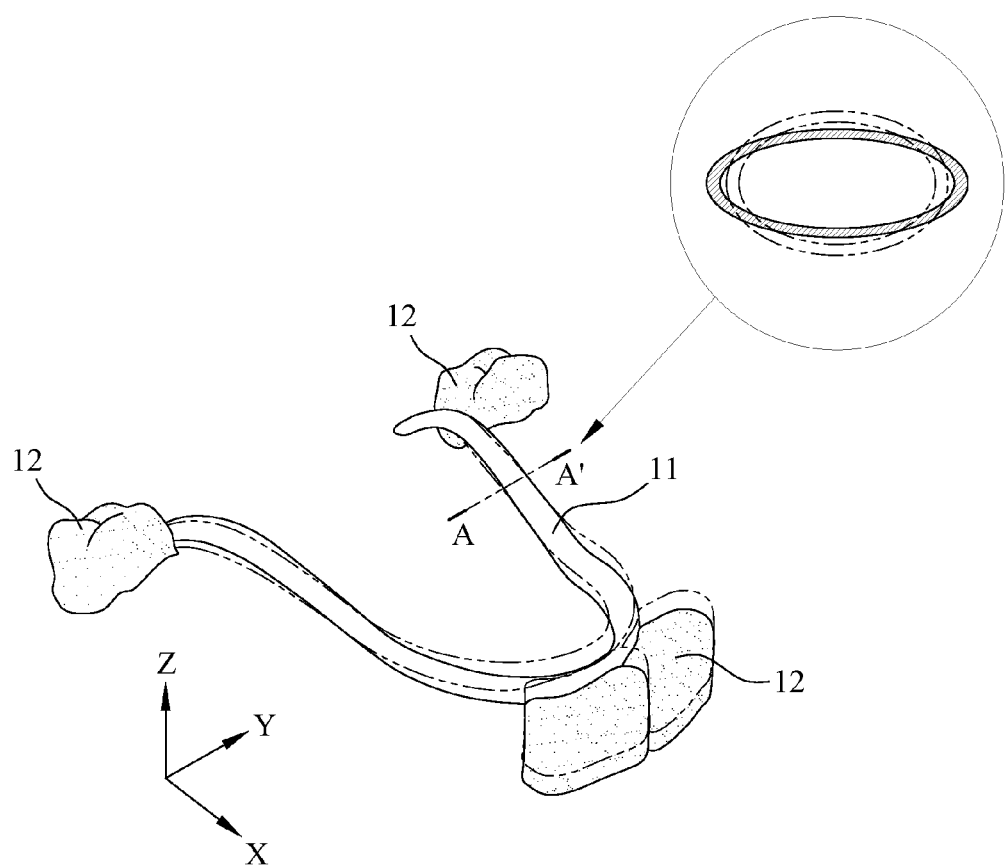
FIG. 4C shows a schematic diagram illustrating the major axis of cross-sectional ellipse set on XY plane, so the deformation will be along Z axis.

The hollow curvilinear actuation structure 11 changes its shape because of the rising of pressure inside, which gradually straightens and flattens the actuation structure 11. This deformation is what the orthodontic treatment needs. In some circumstance, the actuation structure 11 has a spacer inside for dividing the space into a plurality of inner chambers, which equip with a plural of pumping structure 13 accordingly. The cross-section of the pressurized actuation structure 11 of osmotic orthodontic appliance 1 could be locally designed to correspond with the need in orthodontic treatment. In designing the osmotic orthodontic appliance, we define the plane of dentition is XY plane and the cross-section of the pressurized actuation structure 11 is designed as ellipse shape. With the major axis rotating from vertical to parallel relative to XY plane, pressurized actuation structure 11 could be in various shapes which deform in X, Y and/or Z-axis directions. FIGS. 4A-C show that when the cross-section of actuation structure 11 is designed as ellipse shape, the deformation of the three embodiments are determined by the major-axis direction of the ellipse shape. Referring to FIG. 4A, if the major axis of cross-sectional ellipse set to Z axis, the actuation structure 11 will deform on XY plane (the dash lines in the figure represents the shape after deformation, similarly hereinafter); in FIG. 4B, if the major axis of cross-sectional ellipse set to a specific angle relative to Z axis, the actuation structure 11 will increase the deformation along Z axis; FIG. 4C shows the major axis of cross-sectional ellipse set on XY plane, then the deformation will be along Z axis, such that once the osmotic pressure takes effect, the actuation structure 11 deforms along Z axis and moves the front teeth toward Z direction.

Figure 5:
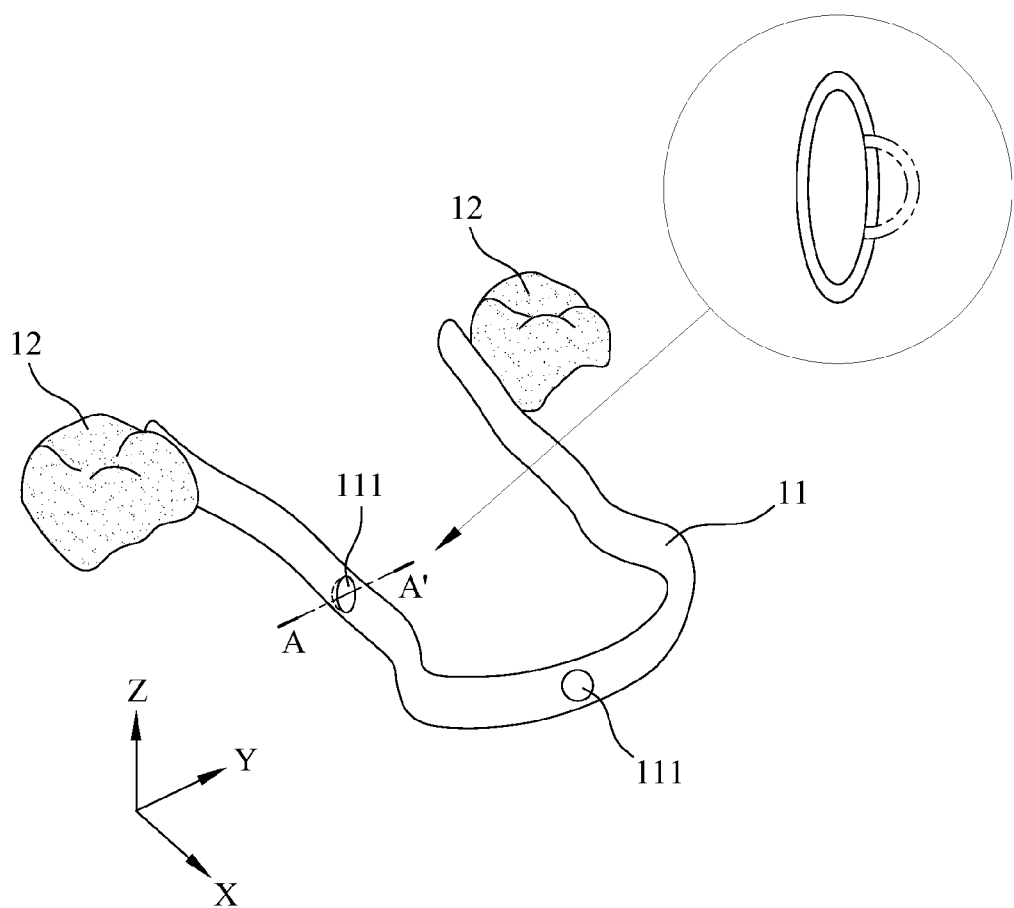
FIG. 5 shows a schematic diagram illustrating the actuation structure having one or more than one inflated structures.

In addition, please refer to FIG. 5, the actuation structure 11 has one or more than one inflated structure 111 used for applying a force to specific teeth. The production method of inflated structure 111 comprises making a hole at a specific position of the actuation structure 11, stuffing a flexible inflated structure 111 (looks like a magic hat) into the hole to maintain the sealed condition in the actuation structure 11 (the brim of the magic hat attaches to the inner surface of the hole), thus the inflated structure 111 uplifts to push the teeth when the pressure inside the actuation structure 11 increases. In an embodiment of the present invention, the inflated structure 111 could be made of polydimethylsiloxane or thermoplastic elastomer.

Because the sizes of teeth, teeth alignment and the shape of oral cavity varying from person to person, the shape of osmotic orthodontic appliance 1 of the present invention is not fixed. It is preferred that the osmotic orthodontic appliance 1 is designed according to the actual teeth alignment and the embodiment described in the previous paragraph. The orthodontic treatment starts with building an original tooth model using a mechanical or optical scanner and a surface construction program. Based on the model, a series of goals for the treatment are determined and the shape of the osmotic orthodontic appliance 1 is designed accordingly. We could fix the osmotic actuation structure 11 on teeth by transparent dental aligner structure 12, for instance, using molar teeth as junction points to anchor the actuation structure 11 and setting junction points on protruded teeth to pull them back or adjust their height, while allowing other teeth to be moved in a relatively unrestricted way. After the shape of the actuation structure 11 is roughly determined, the local cross-sectional shape (including shape and wall thickness) also needs to be determined, to ensure the deformation of the actuation structure 11 is agree with the goals for the treatment. Throughout the designing process, numerical analysis of the stress and strain of the structure is repeatedly performed to optimize the final design. The commercial software which having solid mechanics analysis ability, ANSYS and COMSOL for example, can effectively speed up the design optimization process.

As described above, the present invention provides an osmotic orthodontic appliance 1 that uses osmotic pressure to generate structural deformation, which guides the teeth to move to a desired alignment. The rising water pressure in osmotic orthodontic appliance 1 generates the predetermined deformation. Compared with conventional appliances using shape-memory alloys or plastic aligners, the appliance 1 provides a long-term, steady and adjustable force output for at least one month, while avoids uncomfortable feeling and time delay to the treatment due to the common jump-abruptly-and-drop-slowly force variation.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An osmotic orthodontic appliance, comprising:
   an actuation structure forming a hollow tube filled with a supersaturated solution;
   a dental aligner structure mounted on the actuation structure for fixing the actuation structure on teeth; and
   a pumping structure connected with one end of the hollow tube, comprising a semipermeable device and a supporting structure, wherein the supporting structure supports the semipermeable device.

2. The osmotic orthodontic appliance of claim 1, wherein the hollow tube has a sealing coating on inner surface thereof.

3. The osmotic orthodontic appliance of claim 2, wherein the sealing coating is polydimethylsiloxane.

4. The osmotic orthodontic appliance of claim 1, wherein the actuation structure, the dental aligner structure and the pumping structure are made of a thermoplastic polymer material.

5. The osmotic orthodontic appliance of claim 1, wherein the actuation structure is made of polylactic acid.

6. The osmotic orthodontic appliance of claim 1, wherein the dental aligner structure is made of polyurethane.

7. The osmotic orthodontic appliance of claim 1, wherein the semipermeable device is a semipermeable membrane.

8. The osmotic orthodontic appliance of claim 7, wherein the semipermeable membrane is made of cellulose, aromatic polyamide, polyimide, polyfurane or thermoplastic polyurethane.

9. The osmotic orthodontic appliance of claim 1, wherein the actuation structure has a partially inflated structure.

* * * * *